US00PP21597P2

(12) United States Plant Patent
Kaagman

(10) Patent No.: US PP21,597 P2
(45) Date of Patent: Dec. 28, 2010

(54) ***DAHLIA* PLANT NAMED 'GOLIA DBBRO'**

(50) Latin Name: ***Dahlia* hybrid**
Varietal Denomination: Golia Dbbro

(75) Inventor: Pim Kaagman, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 12/587,133

(22) Filed: Oct. 2, 2009

(51) Int. Cl.
*A01H 5/00* (2006.01)

(52) U.S. Cl. ..... Plt./321

(58) Field of Classification Search ..... Plt./321
See application file for complete search history.

*Primary Examiner*—Susan B McCormick Ewoldt
(74) *Attorney, Agent, or Firm*—S. Matthew Edwards

(57) ABSTRACT

A new *Dahlia* plant named 'Golia Dbbro' particularly distinguished by the large orange-red bi-colored 'collerette' type flowers, full and compact plant habit with excellent branching, medium dark foliage, and good floriferiousness.

1 Drawing Sheet

Latin name of the genus and species of the plant claimed: *Dahlia* hybrid.

Varietal denomination: 'Golia Dbbro'.

BACKGROUND OF THE NEW PLANT

The present invention comprises a new *Dahlia,* botanically known as *Dahlia* hybrid and hereinafter referred to by the variety name 'Golia Dbbro.'

'Golia Dbbro' is a product of a planned breeding program. The new cultivar 'Golia Dbbro' has large orange-red bi-colored 'collerette' type flowers, full and compact plant habit with excellent branching, medium dark foliage, and good floriferiousness.

'Golia Dbbro' originates from a hybridization in a controlled breeding program in Andijk, Netherlands. The pollination took place in August 2006 and the seed sown in November 2006. 'Golia Dbbro' was selected as one flowering plant within the progeny of the stated cross in February 2007 in a controlled environment in Andijk, Netherlands.

The female parent was an unpatented proprietary hybrid seedling identified as 'D05-117-3.' 'D05-117-3' has better flower quality, less intense scarlet and yellow flower color, and more open plant habit than 'Golia Dbbro.'

The male parent of 'Golia Dbbro' was an unpatented proprietary hybrid seedling identified as 'D05-116-3.' 'D05-116-3' has smaller flowers, less intense scarlet and yellow flower color, and a more open plant habit than 'Golia Dbbro.'

The first act of asexual reproduction of 'Golia Dbbro' was accomplished when vegetative cuttings were propagated from the initial selection in February 2007 in a controlled environment in Andijk, Netherlands.

Horticultural examination of plants grown from cuttings of the plant initiated in February 2007 in Andijk, Netherlands, and continuing thereafter, has demonstrated that the combination of characteristics as herein disclosed for 'Golia Dbbro' are firmly fixed and are retained through successive generations of asexual reproduction.

'Golia Dbbro' has not been observed under all possible environmental conditions. The phenotype may vary significantly with variations in environment such as temperature, light intensity and day length.

A Plant Breeder's Right for this cultivar was applied for in Canada in January 2009. 'Golia Dbbro' has not been made publicly available more than one year prior to the filing of this application.

BRIEF DESCRIPTION OF THE PHOTOGRAPHS

Figure 1:
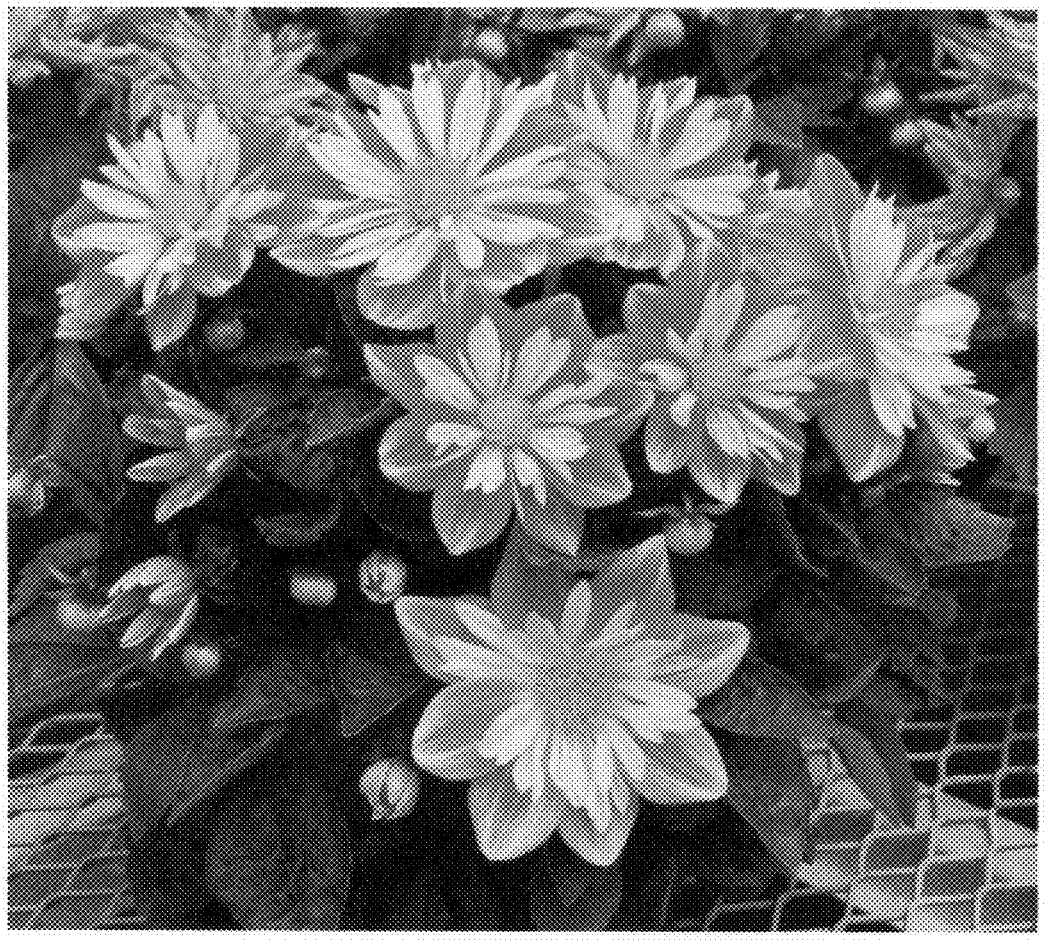
Figure 2:
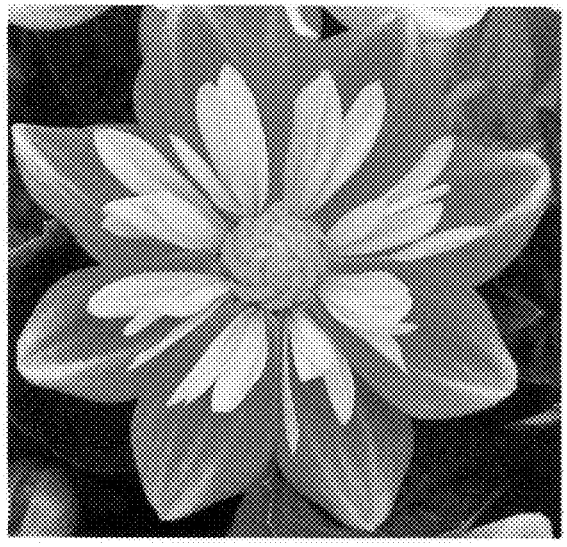

The accompanying photographic drawing shows typical flower and foliage characteristics of 'Golia Dbbro' with colors being as true as possible with an illustration of this type. The photographic drawing shows in FIG. 1, a flowering potted plant of the new variety and in FIG. 2, a close-up of the flowers.

DETAILED BOTANICAL DESCRIPTION

The plant descriptions and measurements were taken in Hillscheid, Germany, in mid-April 2009 on plants that were growing in 12 cm pots on benches in a greenhouse trial, and were about 10-11 weeks old. The aforementioned photographs were taken in early April 2008 in Gilroy, Calif. The plants were growing in bench trials in a greenhouse and were about 12 weeks of age.

Color references are made to The Royal Horticultural Society Colour Chart (R.H.S.) 2001.

BRIEF SUMMARY OF INVENTION

The following traits have been repeatedly observed and are determined to be basic characteristics of the new variety. The combination of these characteristics distinguishes this *Dahlia* as a new and distinct variety.

TABLE 1

DIFFERENCES BETWEEN THE NEW VARIETY 'GOLIA DBBRO' AND A SIMILAR VARIETY

| | 'Golia Dbbro' | 'Golia Oran' (U.S. Plant Pat. No. 19,360) |
|---|---|---|
| General flower color: | RHS 34A | RHS N30A |
| Leaf size: | Narrower and shorter | Wider and longer |
| Stem internode length: | Shorter | Longer |
| Peduncle length: | Shorter | Longer |

Plant:
*Form, growth and habit.*—Compact and mounding, good branching.
*Plant height.*—8-10 cm.
*Plant height (inflorescence included).*—13-14 cm.
*Plant width.*—15-17 cm.
*Garden performance and tolerance to weather.*—Good.
*Crop time to flowering.*—About 9-12 weeks.

Roots:
*Number of days to initiate and develop roots.*—About 21-28 days at about 21 degrees C.
*Type.*—Fine, fibrous, free branching.
*Color.*—RHS N155B but whiter.

Foliage:
*Arrangement.*—Opposite, single, simple.
*Immature, leaf color, upper surface.*—RHS 143B.
*Lower surface.*—Closest to RHS 138C.
*Mature, leaf color, upper surface.*—RHS 137B.
*Lower surface.*—RHS 138B but a little more grayish.
*Length.*—5.0-6.5 cm.
*Width.*—2.3-2.7 cm.
*Shape.*—Elliptical.
*Base shape.*—Attenuate.
*Apex shape.*—Acute to mucronulate.
*Margin.*—Weak crenation, not present on all leaves.
*Texture, upper surface.*—Glabrous, hirsute along the veins.
*Lower surface.*—Glabrous.
*Venation color, upper.*—RHS 144C.
*Lower.*—RHS 144A.
*Petioles color.*—RHS 144C.
*Petioles length.*—0.5-1.3 cm.
*Diameter of petiole.*—0.3 cm at the mid section.
*Texture.*—Smooth, glabrous.

Stem:
*Average quantity of main branches per plant.*—About 15-18.
*Color of stem.*—RHS 143B to RHS 143C.
*Length of stem.*—5-7 cm.
*Diameter.*—0.3-0.4 cm at the midsection.
*Length of internodes.*—1-2 cm.
*Texture.*—Smooth, glabrous.
*Color of peduncle.*—RHS 143B to RHS 143C.
*Length of peduncle.*—Most often 2.5-5.0 cm.
*Peduncle diameter.*—0.2-0.3 cm.
*Texture.*—Smooth, glabrous.

Inflorescence:
*Type.*—Inflorescences borne on terminals above foliage, semi-double flowers.
*Blooming habit.*—Continuous throughout the growing season.
*Average quantity of inflorescences per plant.*—7-8.
*Average quantity of inflorescences per lateral stem.*—1-2.
*Lastingness of individual blooms on the plant.*—7-12 days.
*Fragrance.*—None.

Bud: (just before opening):
*Color.*—RHS 154A to RHS 2A.
*Length.*—1.3-1.4 cm.
*Width.*—1.2 cm.
*Shape.*—Initially round, turning ovate and cylindrical with lengthening of the rays.

Immature inflorescence:
*Diameter.*—4.5-7.0 cm.
*Color of ray florets, upper surface.*—Mainly RHS 33A with RHS 9A in varying sized blotches almost in stripes mainly at the apex.
*Lower surface.*—RHS 33B with RHS 4A in varying sized blotches almost in stripes mainly at the apex.

Mature inflorescence:
*Diameter.*—7.5-8.3 cm.
*Depth.*—2-2.3 cm.
*Total diameter of 'disc'.*—1.3-1.6 cm.
*Receptacle height.*—0.6-0.8 cm.
*Receptacle diameter.*—1.2-1.4 cm.

Ray florets:
*Average quantity of florets.*—About 8.
*Color of florets, upper surface.*—RHS 34A or slightly lighter ground color; RHA 4A apices and varying sized. blotches almost in stripes mainly at the apex end.
*Lower surface.*—RHS 4B with weak striped blotches of about RHS 34C.
*Length.*—3.5-3.9 cm.
*Width.*—1.9-2.1 cm.
*Shape.*—Broadly elliptical.
*Base shape.*—Fused.
*Apex shape.*—Obtuse to slightly mucronulate, but also some almost retuse.
*Margin.*—Entire.
*Texture, upper surface.*—Papillose, glabrous.
*Lower surface.*—Papillose; glabrous.
*Number of petaloids.*—3-5 per ray floret.
*Color of petaloids, upper surface.*—RHS 4A.
*Lower surface.*—RHS 4B.
*Length.*—2.0-2.8 cm.
*Width.*—0.6-0.7 cm.
*Shape.*—Lanceolate to narrowly elliptical.
*Apex shape.*—Acute to obtuse.

Disc florets:
*Average quantity of florets.*—About 35-40.
*Color of florets.*—RHS 5B.
*Length.*—1.1 cm.
*Width.*—0.2-0.3 cm.
*Shape.*—Tube-shaped.
*Apex shape.*—Acute, 5-pointed.

Phyllaries:
*Average quantity.*—About 8.
*Color, upper surface.*—RHS 150C to RHS 154C, but appears almost semi-transparent.
*Lower surface.*—RHS 150C to RHS 154C, but appears almost semi-transparent.
*Length.*—1.5-1.6.
*Width.*—0.6-0.7 cm.
*Shape.*—Ligulate to lanceolate.
*Base shape.*—Fused.
*Apex shape.*—Obtuse.
*Margin shape.*—Entire.
*Texture, upper surface.*—Smooth, glabrous.
*Lower surface.*—Smooth, glabrous.

Reproductive organs:
*Gyneocium.*—Present on both ray and disc florets.
*Pisil quantity.*—1 per floret.
*Length.*—1.3 cm.
*Style color.*—RHS 145C.
*Style length.*—0.6-0.7 cm.
*Stigma color.*—RHS 13A.

*Stigma shape.*—Bi-furchate (bi-lobed).
*Ovary color.*—RHS 144A to RHS 144B.
*Andreocium.*—Present on disc florets only.
*Stamens quantity.*—5 united.
*Color of filaments.*—RHS N155C.
*Length filaments.*—0.3 cm.
*Anther color.*—RHS 13A.
*Anther length.*—0.5-0.6 cm.
*Color of pollen.*—RHS 15A.
*Pollen amount.*—Abundant.
*Fertility/seed set.*—Not observed on this hybrid.

Disease/pest resistance: Disease resistance or susceptibility has not been observed on this hybrid.

What is claimed is:

1. A new and distinct variety of *Dahlia* plant named 'Golia Dbbro,' substantially as illustrated and described herein.

* * * * *